(12) United States Patent
Cohen

(10) Patent No.: US 6,183,254 B1
(45) Date of Patent: Feb. 6, 2001

(54) DENTAL STRAINER UNIT FOR AN ASPIRATOR

(75) Inventor: Howard Cohen, New York, NY (US)

(73) Assignee: East Coast Medical and Dental Devices, Inc., New York, NY (US)

( * ) Notice: Under 35 U.S.C. 154(b), the term of this patent shall be extended for 0 days.

(21) Appl. No.: 09/366,889

(22) Filed: Aug. 4, 1999

(51) Int. Cl.[7] ................................................. A61C 17/06
(52) U.S. Cl. ............................................................... 433/92
(58) Field of Search .................... 433/91, 92; 210/416.1, 210/435, 446, 448, 452

(56) References Cited

U.S. PATENT DOCUMENTS

| | | | |
|---|---|---|---|
| 3,458,050 | * 7/1969 | Cooper | 210/448 |
| 3,476,144 | 11/1969 | Krantz . | |
| 3,890,712 | 6/1975 | Lopez . | |
| 4,058,897 | * 11/1977 | Edwards | 433/92 |
| 4,083,706 | * 4/1978 | Wiley | 433/92 |
| 4,417,874 | 11/1983 | Andersson et al. . | |
| 4,894,156 | * 1/1990 | Murken | 210/448 |
| 5,066,228 | 11/1991 | Doundoulakis et al. . | |
| 5,094,616 | 3/1992 | Levenson . | |
| 5,407,565 | * 4/1995 | Austin, Jr. et al. | 433/92 |
| 5,536,402 | * 7/1996 | Kluhsman | 210/448 |
| 5,624,559 | * 4/1997 | Levin et al. | 210/448 |
| 5,630,939 | * 5/1997 | Bulard et al. | 433/92 |
| 5,741,134 | * 4/1998 | Davis | 433/91 |
| 5,796,035 | * 8/1998 | Walker | 210/448 |

OTHER PUBLICATIONS

1997 Catalog of Products, Quality Aspirators, Duncanville TX (4 pages).

* cited by examiner

*Primary Examiner*—Todd E. Manahan

(57) ABSTRACT

A dental strainer unit includes a plastic strainer, a plastic strainer cap, and a transparent, non-rigid plastic housing. The strainer unit can be cost-effectively manufactured and easily disassembled and cleaned. The strainer cap can be manufactured in a variety of sizes to permit different aspirator devices to be attached thereto, and the housing can be snap-fit over the enlarged head of a saliva ejector valve. The dental strainer unit can be used in a modularized dental aspiration system.

10 Claims, 5 Drawing Sheets

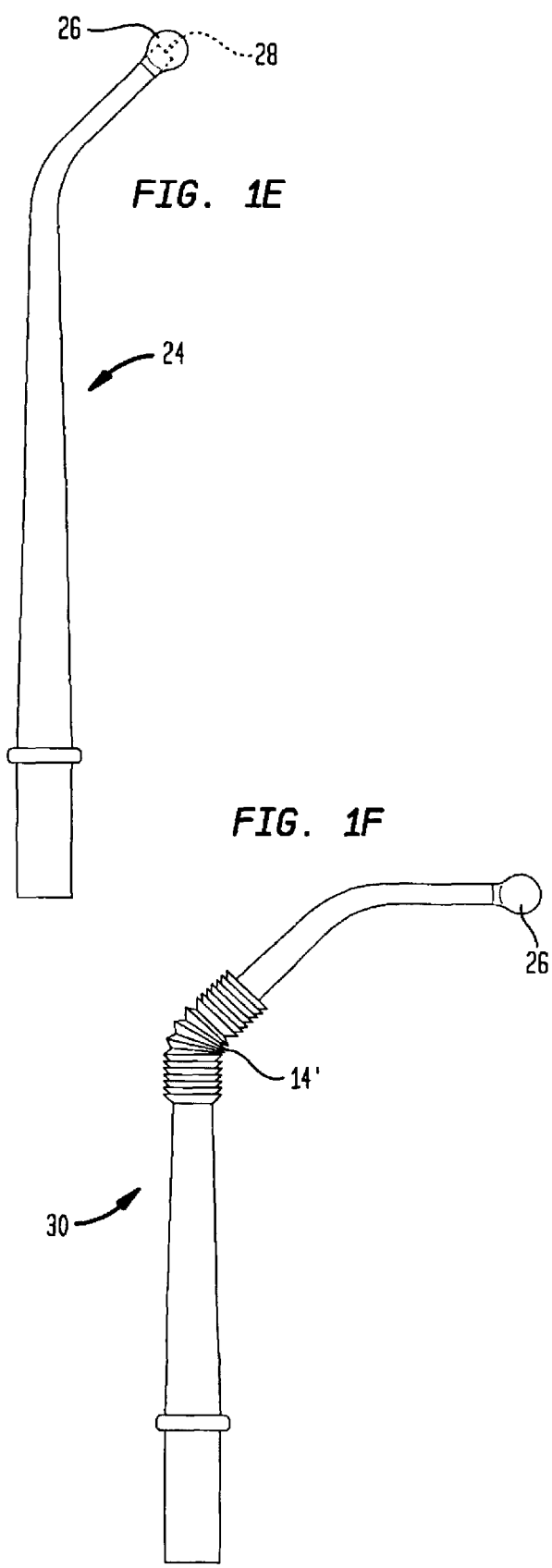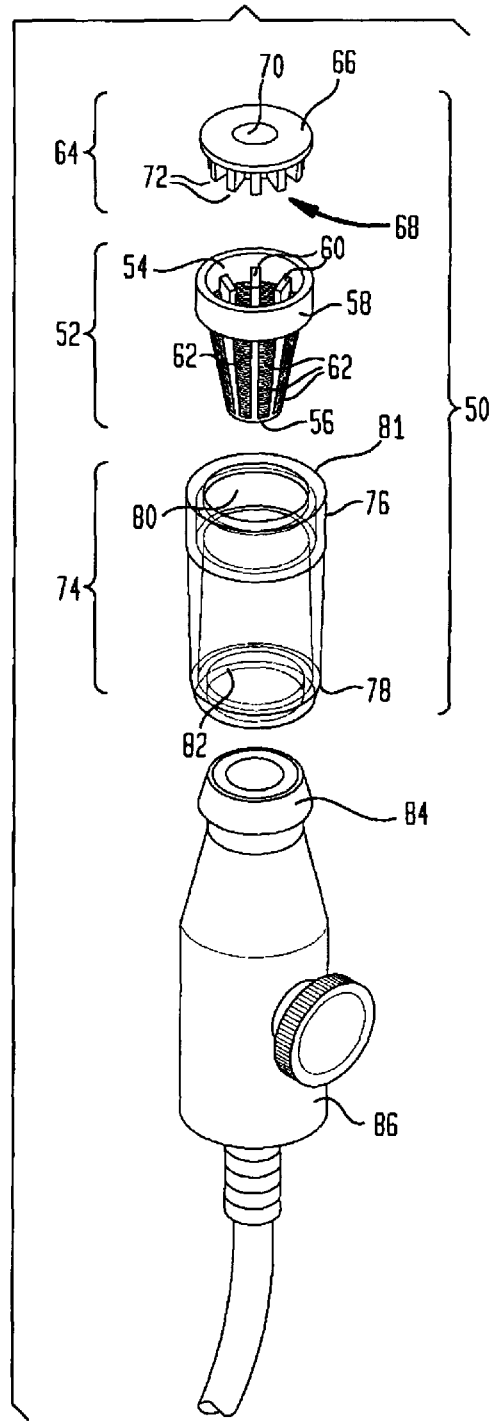

DENTAL STRAINER UNIT FOR AN ASPIRATOR

BACKGROUND OF THE INVENTION

The invention relates to aspirator apparatus, and more particularly relates to aspirator apparatus of the vacuum-operated type. In its most immediate sense, the invention relates to dental aspiration devices such as are used to aspirate body fluids and solids from a patient's mouth, and to methods for using such devices.

Dental procedures can cause solid matter (e.g. bone chips, tooth particles, tissue fragments, pieces of amalgam etc.) to enter fluids (e.g. saliva, blood, and cooling water) that are present in the patient's mouth. The solid matter is removed from the mouth to prevent the patient from swallowing or aspirating it, and removal of the solid matter necessarily entails removal of the fluids as well. When such fluids are withdrawn from the patient's mouth (as by a vacuum-powered saliva ejector or a high-speed saliva aspirator) this solid matter can cause difficulties for the dentist and even for the patient. One such difficulty is that the solid matter can clog the vacuum system. Another such difficulty is that the solid matter can build up upon the inside surfaces of the vacuum lines, thereby forming a base for the growth of biofilm that in turn promotes the growth of bacteria. For these reasons, it is known to provide a strainer unit behind the ejector or aspirator. The strainer unit separates the solid matter from the body fluids, protecting the vacuum system and making it more difficult for a biofilm to build up. Conventionally, the ejector or aspirator is disposable, but the strainer unit is not.

Existing strainer units have a number of disadvantages. First, existing FDA regulations do not require that strainer units be sterile; they need only be clean. And, even if a particular dentist is motivated to sterilize a strainer unit before connecting it to the vacuum system, existing strainer units can neither be easily emptied nor easily cleaned and sterilized. Hence, a strainer unit used during a dental procedure on a patient will likely be unsterile at the beginning of the procedure. In the worst case, the strainer unit will contain solid matter and/or body fluids from a prior patient. This poses the danger that bodily substances from a dental procedure performed earlier in a day may cross-contaminate (as by backflowing fluid into the patient's mouth) a patient undergoing a dental procedure later on that day. Second, existing strainer units are not versatile. (The saliva ejector shown in U.S. Pat. No. 3,890,712 is an example of such a non-versatile device.) They are designed to work only with a particular type of saliva ejector or aspirator, and cannot easily be used with another type. Third, existing strainer units are relatively expensive. (The Osseous Coagulum Trap now being sold through Quality Aspirators, Duncanville Tex., is an example of an expensive strainer unit.) Hence, if a dentist is motivated to use a sterile strainer unit for each patient, the dentist must make a considerable investment in strainer units and must incur increased operating expenses to clean and to sterilize them.

It would be advantageous to provide an improved strainer unit that would overcome these disadvantages.

Existing saliva ejectors and high-speed saliva aspirators also have disadvantages. One conventional saliva ejector, which has a strainer tip at its distal end, can become painfully embedded in the soft tissue of the patient's mouth. This is because the patient's flesh can seal off the holes in the strainer tip. When this happens, the vacuum to the saliva ejector causes the strainer tip and the patient's flesh to be tightly urged against each other. Similarly, a conventional high-speed saliva aspirator can likewise become wedged against the patient's flesh and cause damage to the tissue.

Finally, although conventional saliva ejectors, saliva extractors and similar dental tools are supplied in a "clean" state, they necessarily become less clean when contacted by the hand of the dentist or dental hygienist.

It would be advantageous to provide a saliva ejector and a saliva extractor, and a method for using such dental tools, that would overcome these disadvantages.

In accordance with the invention, a modularized aspiration system is provided. One component of the system is an all-plastic strainer unit. This strainer unit has three parts: a plastic strainer, a plastic strainer cap, and a plastic housing. The strainer has an open inlet end and an outlet end and a multiplicity of openings sized to permit fluids to pass out of the strainer and to retain solids within the strainer. The retainer cap is attached to the strainer and covers its inlet end, and has an inlet port where an aspirator device (such as a saliva ejector or a high-speed saliva aspirator) can be attached. The housing has an inlet end and an outlet end. The inlet end is shaped to receive the strainer so that the inlet end of the strainer faces the inlet end of the housing and the outlet end of the strainer faces the outlet end of the housing. The outlet end has an outlet port sized to fit onto a distal end of a conventional vacuum valve.

In preferred embodiments, the strainer unit is a dental strainer unit, the vacuum valve is a saliva ejector valve, the openings are sized to permit saliva, blood, and water to pass out of the strainer, and the strainer cap and strainer are removably secured within the housing. This makes it possible to adapt the strainer unit for attachment to almost any saliva removal device by mounting the strainer unit with a cap having an appropriately-sized male or female element. This also makes it possible to manufacture the strainer unit economically, since the number of parts required is small; the same strainer and housing can be used in all instances and only the cap (which is a comparatively small and inexpensive part) need be made in a variety of sizes.

Advantageously, and in preferred embodiments, the housing is transparent and non-rigid; transparency allows the dentist or dental hygienist to know if the strainer is becoming overfull, and non-rigidity allows the strainer unit to be positively snap-fit over the enlarged head of a conventional saliva ejector valve (and to thereby positively notify the dentist or hygienist that the attachment between the valve and the housing is proper). To make the strainer unit more generally useful, it is possible to provide an elongated adaptor having one end with the shape of a saliva ejector valve head and the other end shaped to mate with a high-volume valve. The preferred embodiment of a strainer unit in accordance with the invention forms the basis for a versatile modular system and can be used to connect virtually any type of saliva removal device with any conventional vacuum source. Further advantageously, and in preferred embodiments, the strainer is generally frustum-shaped, with its inlet end at the base of the frustum.

Further advantageously, in accordance with the invention an improved saliva ejector and an improved high-speed saliva aspirator are provided. In a flexible saliva ejector in accordance with the invention, a protective flange is provided adjacent to, and spaced apart from, the strainer tip that is conventionally provided. This prevents the patient's flesh from blocking all the holes through which fluids are removed from the patient's mouth, and thereby prevents the saliva ejector and the patient's flesh from being tightly and painfully urged together by the vacuum. In a saliva extractor in accordance with the invention, a protective flexible tip is secured at the distal end. This cushions the patient's flesh at the point where it is contacted by the distal end of the saliva extractor, making it less likely that the distal end of the extractor will injure the patient.

In preferred embodiments, a saliva ejector and a saliva extractor in accordance with the invention are pleated, as with locking bellows. This makes it easier for the device to maintain the shape desired without the use of stiffening wire in the wall of the device.

Still further advantageously, in accordance with the invention a new method of operating a hand-operated dental instrument (such as a high volume valve or a saliva ejector valve) is provided. In accordance with this method, a dental tool (such as a saliva ejector or a high-speed saliva aspirator in accordance with the invention, with or without a strainer unit in accordance with the invention) is packaged within a pouch, advantageously a conventional sterilizing pouch. If the dentist so desires, he can sterilize the tool and the strainer unit inside the pouch before using them. One end of the pouch is then opened to permit the instrument to be introduced into the pouch and connected with the tool. Then, the other end of the pouch is opened so the tool can be pushed out of the pouch and used in a dental operation. The tool is pushed out until the instrument is sheathed within the pouch, where it can be operated through the pouch without being physically touched by the dentist or dental hygienist. In this way

BRIEF DESCRIPTION OF THE DRAWINGS

The invention will be better understood with reference to the following illustrative and non-limiting drawings, in which:

FIG. 1E shows a high-speed saliva aspirator in accordance with a first embodiment of the invention;

FIG. 1F shows a high-speed saliva aspirator in accordance with a second embodiment of the invention;

FIG. 2 is an exploded view of a preferred embodiment of a strainer unit in accordance with the invention;

DETAILED DESCRIPTION OF PREFERRED EMBODIMENTS

The same elements are always indicated by the same reference numbers in all the Figures. The Figures are not necessarily to scale and dimensions of certain parts may be exaggerated for clarity. Corresponding elements of different embodiments have the same reference number, but are distinguished by the use of primes.

Figure 1D:
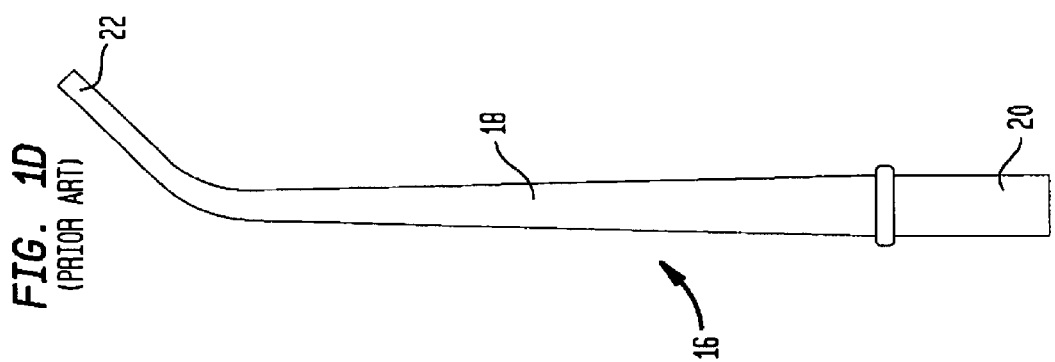
FIG. 1D shows conventional high-speed saliva aspirator.
Figure 1C:
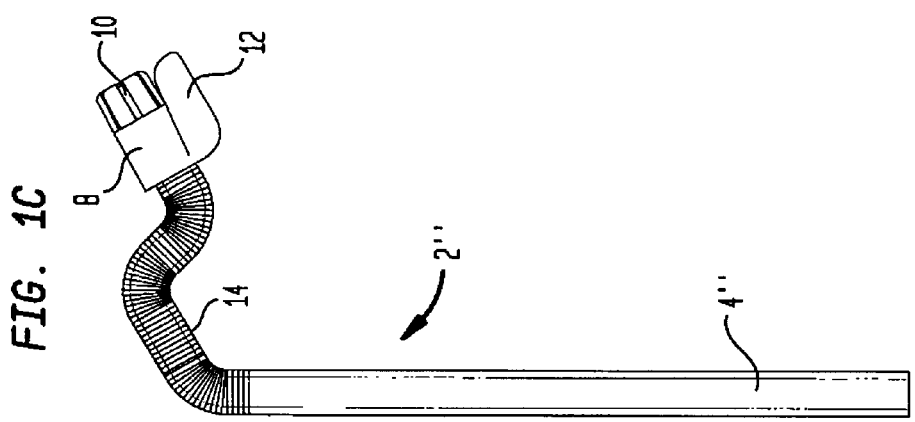
FIG. 1C shows a saliva ejector in accordance with a second preferred embodiment of the invention.
Figure 1B:
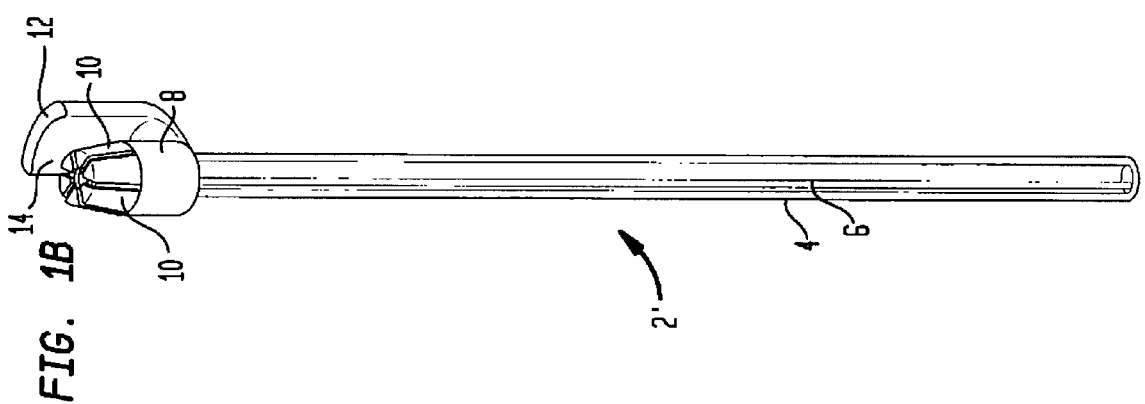
FIG. 1B shows a saliva ejector in accordance with a first preferred embodiment of the invention.
Figure 1A:
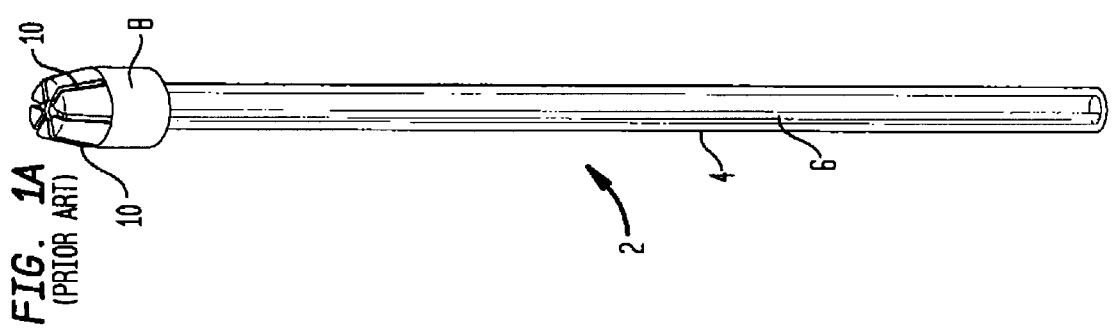
FIG. 1A shows a conventional saliva ejector.

FIG. 1A shows a conventional saliva ejector generally indicated by reference number 2. This has a flexible tube 4 of transparent or opaque plastic. A bendable wire 6 is embedded in the tube 4; this keeps the tube 4 in the position into which it is bent.

The ejector 2 has a strainer tip 8 at its distal end. The strainer tip 8 has a plurality of radially extending slots 10 that permit body fluids and small solid objects (bone, tooth debris, tissue, dental amalgam etc.) to be withdrawn through the tube 4 via a vacuum.

If the strainer tip 8 is introduced into a small recess in the patient's mouth (not shown) while the vacuum is turned on, the patient's flesh (not shown) can block off some the slots 10 at the same time. This causes the tip 10 and the patient's flesh to press tightly against each other, and can be painful.

A saliva ejector 2' in accordance with the preferred embodiment of the invention as illustrated in FIG. 1B has the same tube 4, wire 6, and strainer tip 8 with slots 10. However, a protective flange 12 is located adjacent to the tip 8 but spaced apart from it by a relatively small distance. Advantageously but not necessarily, the flange 12 is made of the same material as the tip 8, is molded integrally with it, and is molded so that the gap 14 between the flange 12 and the tip 8 is of constant width, but this is not required.

Because the flange 12 is spaced apart from the tip 8 by a relatively small distance, it is unlikely that a flap of the patient's flesh can be interposed between the tip 8 and the flange 12. For this reason, any slot(s) 10 that are located in the region of the flange 12 will likely always remain unblocked, so that the tip 10 and the flange 12 never become tightly wedged against the patient's flesh.

In accordance with the preferred embodiment of a saliva ejector 2', the flange 12 is diametrically opposed to the wire 6. The location of the flange 12 therefore identifies the location of the wire 4 within the tube. This permits the dentist or dental hygienist to bend the tube 4 so that the wire 6 is on the outside, even if the tube 4 is made of opaque material.

FIG. 1C shows a second preferred embodiment of a saliva ejector 2". The saliva ejector 2" has the same tube 4, tip 8 and flange 12 as the second preferred embodiment, but there is no wire in the tube 4 and the tube 4 is pleated with thin, flexible pleats 14. The pleats are formed as locking bellows. (Such pleats 14 are known by themselves; they are similar in nature to the pleats provided in plastic beverage straws.) By using pleats 14 formed as locking bellows, the saliva ejector 2" maintains its desired shape in use, and a stiffening wire (such as 6) is not required.

FIG. 1D shows a conventional high-speed saliva aspirator generally indicated by reference number 16. This has an elongated rigid plastic tube 18 that tapers down from a larger proximal end 20 to a smaller distal end 22. Such an aspirator 16 can injure or cause pain to the patient (not shown) if the distal end 22 is occluded by the patient's flesh while the vacuum is on.

To reduce the likelihood that such injury or pain will result, a first preferred embodiment of a high-speed saliva aspirator 24 in accordance with the invention (see FIG. 1E) has a protective flexible tip 26 attached around its distal end. Advantageously although not necessarily, the tip 26 is a solid drop of an elastomeric polymer and has a small port 28 through which the patient's body fluids may be withdrawn. For visibility, the tip 26 is colored to contrast with the color of the patient's flesh.

A second preferred embodiment of a high-speed saliva aspirator 30 in accordance with the invention (see FIG. 1F) has pleats 14' intermediate its ends. The pleats 14', like the pleats 14, are formed as locking bellows. These make it possible for the dentist or dental hygienist to put the aspirator 30 in a more convenient shape.

A preferred embodiment of an all-plastic strainer unit generally indicated by reference number 50 is shown in FIG. 2. The strainer unit 50 has a plastic strainer generally indicated by reference number 52. The strainer 52 is advantageously but not necessarily a unitary part made of polyethylene or styrene; these materials are easy to mold and can be sterilized. The strainer 52 is generally frustum-shaped; it is open at its base 54 (which is the input end) and may be open or closed at its apex 56. A short tubular collar 58 is provided at the base 54, and ribs 60 extend radially inwardly into the strainer 52 between the collar 58 and the apex 56. A multiplicity of openings 62 are provided; in this example the openings 62 are rectangular and extend in parallel arrays between adjacent ribs 60, but this is not required and any other suitable pattern could be used instead. The openings 62 are sized to permit body fluids (e.g. saliva and blood) to pass out of the interior of the strainer 52 while retaining solid matter (not shown) inside it.

A strainer cap generally indicated by reference number 64 fits into the collar 58. The cap 64 is advantageously a unitary part likewise made of polyethylene or styrene, but this is not required. The outside portion 66 of the cap 64 is an annulus that supports an inside portion 68 and that has a central inlet port 70. In this example, the inside portion 68 is formed of a plurality of radially-extending arms 72, but this is merely for convenience; it could be formed otherwise.

The dimensions of the cap 64 are chosen so that the periphery of the inside portion 68 is a circle that is only slightly larger than the inside of the collar 58. As will be seen below, this slightly expands the collar 58 so as to hold the cap 64 securely in the strainer 52 and to hold the strainer 52 within the housing 74 described below. The inlet port 70 is dimensioned to permit a saliva removal device (such as the above-described preferred embodiments of the saliva ejector 2 and 2") to be attached to the cap 64 (as by insertion and friction-fitting therein) and to permit body fluids and foreign bodies to be drawn into the strainer 52. As will be seen below, the cap 64 is an adaptor; different saliva removal devices are attached to the strainer unit 50 by using differently shaped caps 64.

A housing 74 is a unitary piece that is advantageously transparent and made of any suitable elastomeric polymer that is transparent when cured. (Transparency allows the dentist or the dental hygienist to see if the strainer unit 50 is becoming overfull or is operating improperly; it is advantageous but not required. As used herein, "transparency" refers to the ability of a dentist or dental hygienist to generally determine the amount of material inside the housing 74; it is not necessary that the housing 74 be as clear as glass.) The housing 74 is generally cylindrical, but in this example the inlet end 76 is slightly larger than the outlet end 78.

At the very end of the outlet end 78 is located a lip 81. The interior surface of the inlet end 76 is advantageously a slightly enlarged tubular collar 80 that has the same width as the collar 58 but a slightly smaller diameter than the exterior diameter of the collar 58. The lip 81 and the collar 80 serve to fix the cap 64 and the strainer 52 inside the housing 74 so they neither slip out of the housing 74 nor slide inside it. In use, the strainer 52 is inserted past the lip 81 into the housing 74 until the strainer 52 slides in as far as it can go. The slight oversize of the collar 58 relative to the collar 80 makes an interference fit inside the housing 74. Then, the cap 64 is snapped in just below the lip 81. In this position, the inside portion 68 of the cap 64 is pressed into the collar 58 and the cap 64 and the strainer 52 are locked in place inside the housing 74.

Figure 3C:
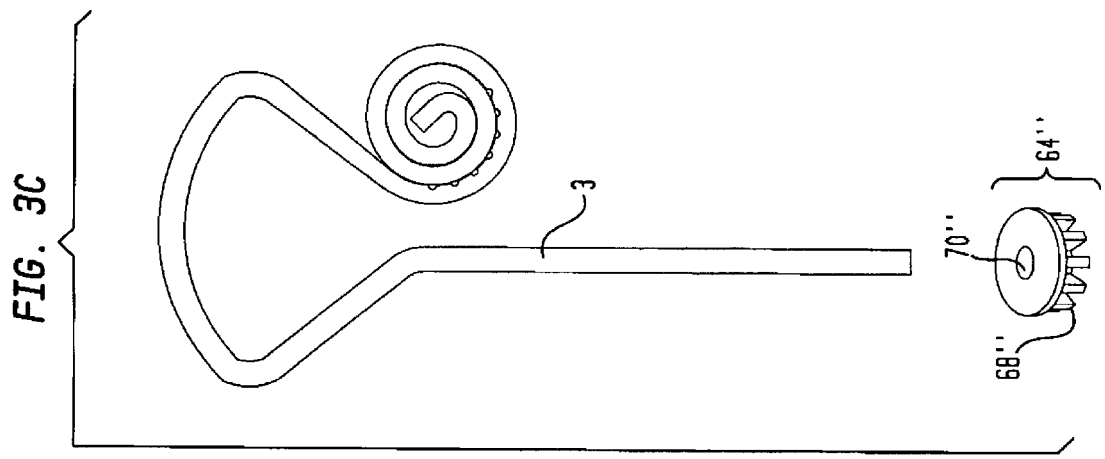
FIG. 3C shows how another type of saliva ejector can be mounted to a strainer unit in accordance with the preferred embodiment of the invention.
Figure 3B:
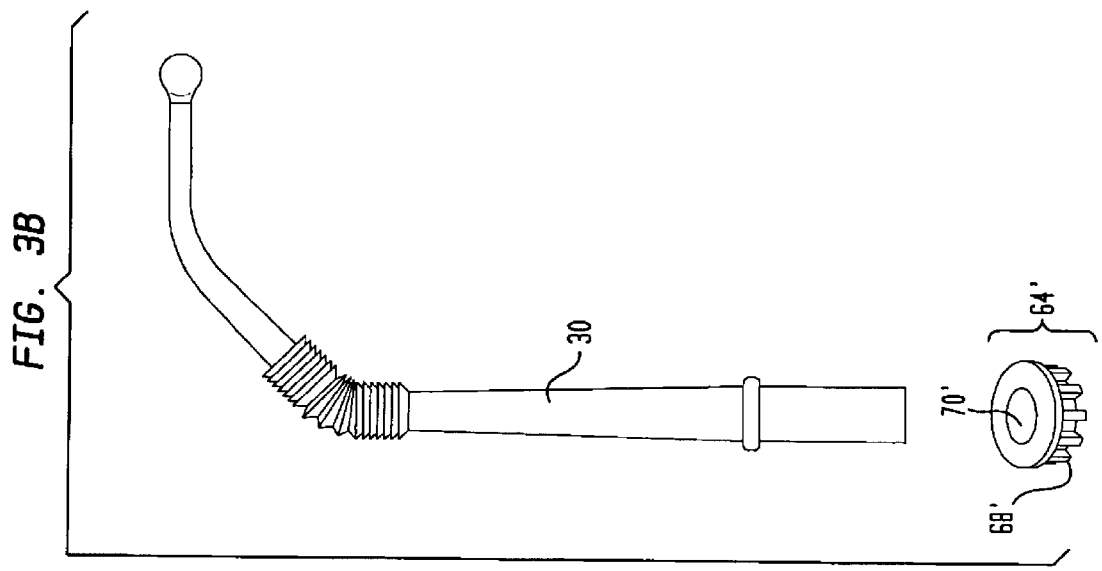
FIG. 3B shows how a preferred embodiment of a high-speed saliva aspirator in accordance with the invention can be mounted to a strainer unit in accordance with the preferred embodiment of the invention.
Figure 3A:
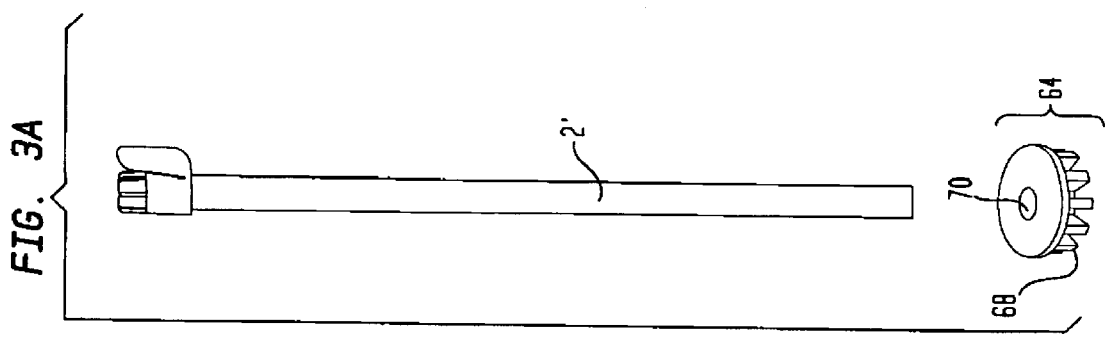
FIG. 3A shows how a preferred embodiment of a saliva ejector in accordance with the invention can be mounted to a strainer unit in accordance with the preferred embodiment of the invention.

FIGS. 3A, 3B, and 3C are exemplary illustrations showing how different saliva removal tools can be attached to the strainer unit 50 by using different caps 64, 64', and 64". FIG. 3A shows how the saliva ejector 2' can be attached to the strainer unit 50 using a cap 64. FIG. 3B shows how the high-speed saliva aspirator 30 can be attached to the strainer unit by using a different cap 64', and FIG. 3C shows how another type of saliva ejector 3 can be attached to the strainer unit 50 using a different cap 64".

Figure 4A:
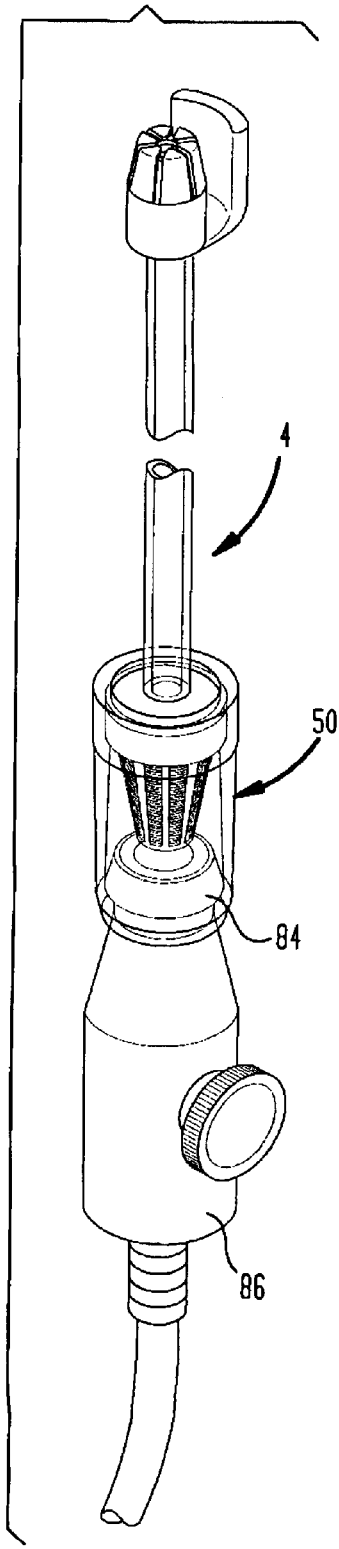
FIG. 4A shows how a strainer unit in accordance with the invention may be attached between a saliva ejector and a saliva ejector valve.
Figure 4B:
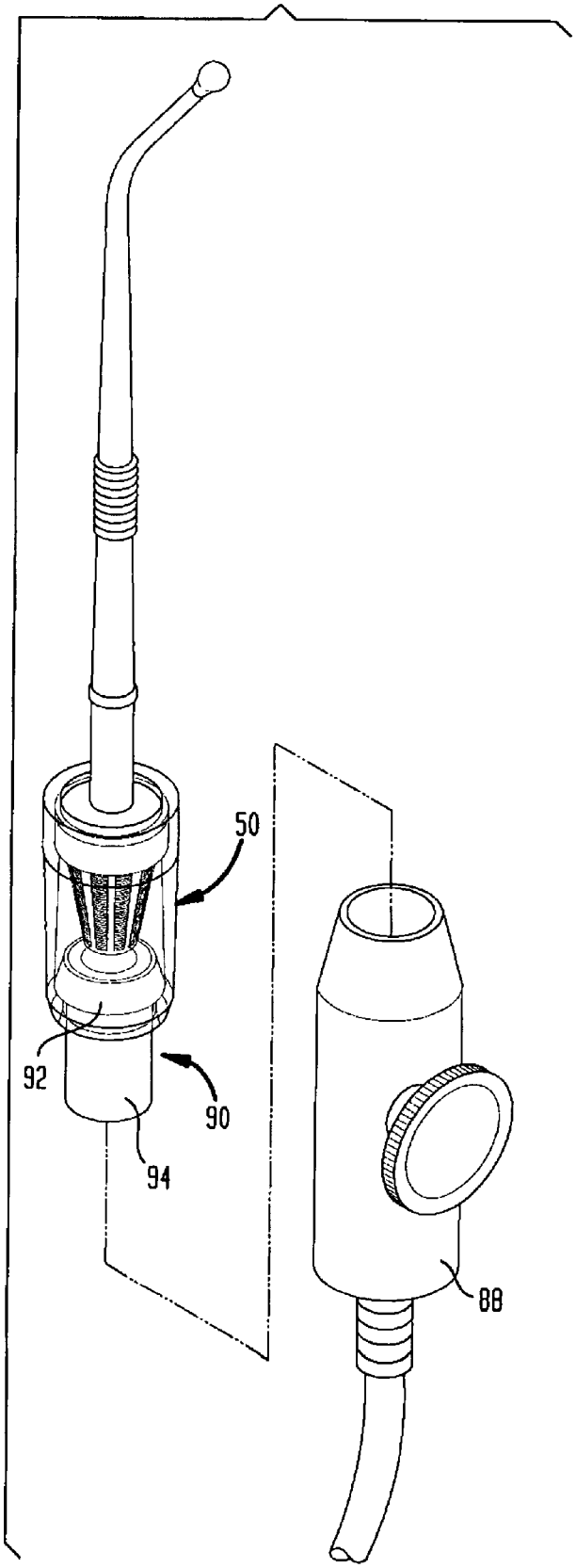
FIG. 4B shows how a strainer unit in accordance with the invention may be attached between a high-speed saliva aspirator and a high-volume valve using an adaptor.

At the extreme end of the outlet end 78 is an annular lip 82. The lip 82 is dimensioned so that the outlet end 78 can be snap-fit over the enlarged head 84 of the distal end of a saliva ejector valve 86. Alternatively, if the strainer unit 50 is to be connected to a high-volume valve 88 (FIG. 4B), an adaptor generally indicated by reference number 90 can be used. The adaptor 90 has an enlarged end 92 that has the same shape as the head 84 of a saliva ejector valve and a smaller end 94 that is dimensioned to fit within a conventional high-volume valve 88. Hence, if the strainer unit 50 is to be used with a saliva ejector 2 or 2', the strainer unit 50 can be connected directly to a saliva ejector valve 88 (FIG. 4A). If, alternatively, the strainer unit 50 is to be used with a high-speed saliva aspirator 16 or 24, the strainer unit can be attached to a high-volume valve 86 via an adaptor 90 (FIG. 4B). If a high-volume valve 86 becomes clogged, a high-speed saliva aspirator (e.g. 16 or 24) can be supplied with vacuum via a saliva ejector valve 88; likewise, if a saliva ejector valve 88 becomes clogged, a saliva ejector 2 or 2' can be supplied with vacuum via a high-volume valve 86.

The method illustrated in FIGS. 5A–5D is shown using a tool 100, which generally indicates a saliva ejector 2' in accordance with a preferred embodiment of the invention connected to a strainer unit 50 in accordance with a preferred embodiment of the invention. This is only exemplary, and any other dental tool can be used instead.

Figure 5A:
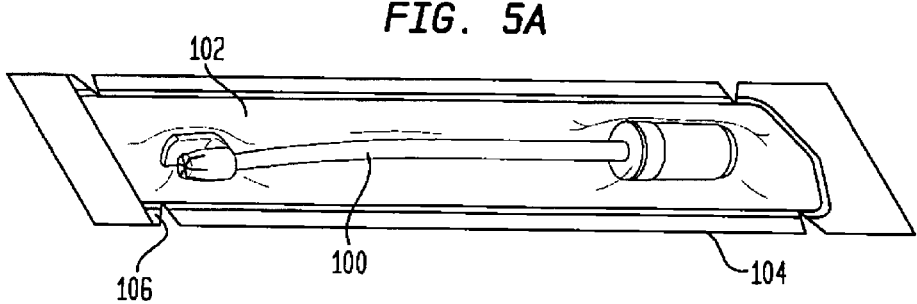
FIGS. 5A–5D show a method of operating a dental tool in accordance with the preferred embodiment of the invention.
Figure 5B:
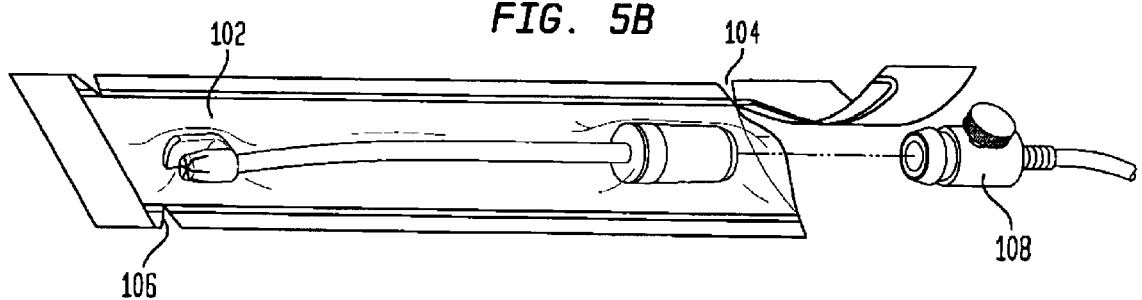
Figure 5C:
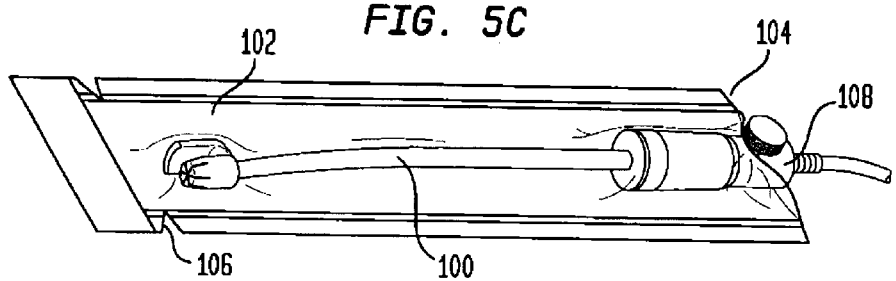
Figure 5D:
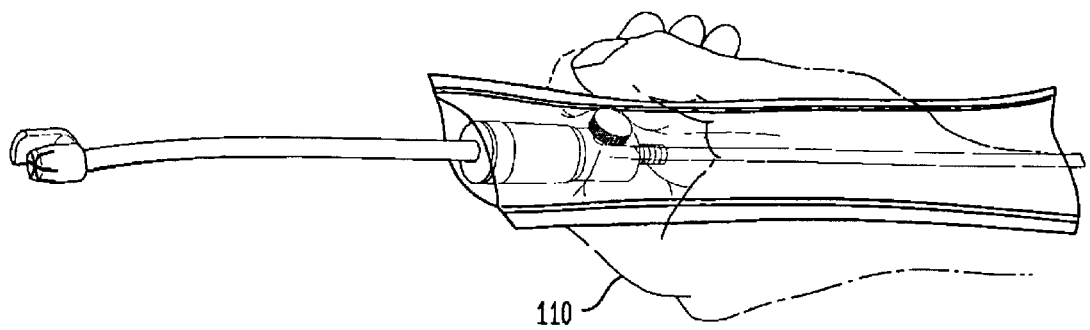

The tool 100, in a clean or (optionally, and preferably) sterile state, is packaged inside a conventional sterilizing pouch 102, with openable ends 104 and 106. Initially, the end 104 is opened (FIG. 5B), which permits a hand-operable dental instrument 108 (in this instance, the instrument 108 is a saliva ejector valve but this is not required) to be attached to the tool 100 (FIG. 5C). Then, the end 106 is opened, permitting the pouch 102 to be slid down so as to expose the distal end of the tool 100 while covering the instrument 108 (FIG. 5D). The tool 100 can be used in a dental operation while the instrument 108 is operated through the pouch, thereby preventing the tool from becoming unsterile as a result of contact with the hand 110 of the dentist or dental hygienist.

Although at least one preferred embodiment of the invention has been described above, this description is not limiting and is only exemplary.

The scope of the invention is defined only by the claims, which follow:

1. A dental strainer unit for use with an aspirator, comprising:

a plastic strainer having an open inlet end and an outlet end, the outlet end having a multiplicity of openings sized to permit saliva, blood and water to pass out of the strainer and to retain solids within the strainer;

a plastic strainer cap attached to the strainer and covering the inlet end thereof, the cap having an inlet port where an aspirator device can be attached; and a transparent, non-rigid plastic housing having an inlet end and an outlet end, the inlet end being shaped to receive the strainer and strainer cap so that the inlet end of the strainer faces the inlet end of the housing, the outlet end of the strainer faces the outlet end of the housing, and the strainer and strainer cap are removably secured within the housing, the outlet end of the housing having an outlet port sized to snap-fit over an enlarged head at a distal end of a conventional saliva elector valve.

2. The strainer unit of claim 1, wherein the strainer is generally frustum-shaped and has a base and an apex, and wherein the inlet end is located at the base.

3. A prepackaged disposable saliva aspirator assembly, comprising:

the dental strainer unit of claim 1;

an aspirator device attached to the plastic strainer cap; and a pouch enclosing the dental strainer unit and aspirator device.

4. The assembly of claim 3, wherein the dental strainer unit and aspirator device are sterile.

5. The assembly of claim 3, wherein the aspirator device is of plastic.

6. A method of using the assembly of claim 3, comprising:

opening an end of the pouch adjacent the outlet port of the dental strainer unit;

snap-fitting the outlet port of the dental strainer unit over the enlarged head of a saliva ejector valve;

opening another end of the pouch adjacent the aspirator device; and sliding the pouch to expose the aspirator device.

7. In combination:

a plastic frustrum-shaped strainer having an open inlet end at its base and an outlet end at its apex, the outlet end having a multiplicity of openings sized to permit saliva, blood, and water to pass out of the strainer and to retain solids within the strainer;

a plastic strainer cap attached to the strainer and covering the inlet end thereof, the cap having an inlet port where an aspirator device can be attached;

a transparent, non-rigid plastic housing having an inlet end and an outlet end, the inlet end being shaped to receive the strainer and the strainer cap so that the base of the strainer faces the inlet end of the housing and the apex of the strainer faces the outlet end of the housing and the strainer and the strainer cap are removably secured within the housing, the outlet end of the housing having an outlet port sized to snap-fit over an enlarged head at a distal end of a conventional saliva ejector valve; and an aspirator device attached to the strainer cap at the inlet port thereof.

8. The combination of claim 7, wherein the aspirator device is a saliva ejector.

9. The combination of claim 8, wherein the aspirator device is a high-speed saliva aspirator.

10. A dental strainer unit for use with an aspirator, comprising:

a plastic strainer having an open inlet end and an outlet end, the outlet end having a multiplicity of openings sized to permit fluids to pass out of the strainer and to retain solids within the strainer;

a plastic strainer cap attached to the strainer and covering the inlet end thereof, the cap having an inlet port where an aspirator device can be attached; and a non-rigid plastic housing having an inlet end and an outlet end, the inlet end being shaped to receive the strainer so that the inlet end of the strainer faces the inlet end of the housing and the outlet end of the strainer faces the outlet end of the housing, the outlet end of the housing having an outlet port sized to snap-fit over the enlarged head of a conventional vacuum valve.

* * * * *